United States Patent [19]
Schwartz et al.

[11] Patent Number: 5,437,288
[45] Date of Patent: Aug. 1, 1995

[54] FLEXIBLE CATHETER GUIDEWIRE

[75] Inventors: Robert S. Schwartz, Rochester, Minn.; David Berry, Longmont, Colo.; Frederick S. Halverson, North Oaks; James V. Donadio, III, Chaska, both of Minn.

[73] Assignee: Mayo Foundation for Medical Education and research, Rochester, Minn.

[21] Appl. No.: 940,523

[22] Filed: Sep. 4, 1992

[51] Int. Cl.⁶ ............................................. A61B 5/00
[52] U.S. Cl. .................................. 128/772; 128/657; 604/280; 604/282
[58] Field of Search ............... 128/657, 772; 604/280, 604/282, 95, 170

[56] References Cited

U.S. PATENT DOCUMENTS

| | | | |
|---|---|---|---|
| 4,719,924 | 1/1988 | Crittenden et al. | 128/657 X |
| 4,763,647 | 8/1988 | Gambale | 128/657 |
| 4,925,445 | 5/1990 | Sakamoto et al. | |
| 5,003,989 | 4/1991 | Taylor et al. | 128/772 |
| 5,047,018 | 9/1991 | Gay et al. | 128/657 X |
| 5,069,226 | 12/1991 | Yamauchi et al. | |
| 5,095,915 | 3/1992 | Engelson | 128/772 |
| 5,133,364 | 7/1992 | Palermo et al. | 128/772 |

FOREIGN PATENT DOCUMENTS 4104092 8/1991 Germany .
WO91/15152 10/1991 WIPO .
92/19151 11/1992 WIPO ................................ 128/772

OTHER PUBLICATIONS

Mooney et al., *The Ultra-Select Guidewire: A New Nitinol Guidewire for Coronary Angioplasy*, J. Inv. Card., Sep./Oct. 1991, vol. 3, No. 5, p. 242.

Stice, *The Use of Superelasticity in Guidewires and Arthroscopic Instrumentation*, Engineering Aspects of Shape Memory Alloys, Butterworth-Heinemann Ed., T. W. Duerig et al., p. 483, 1990.

Cole-Parmer Instrument Company, 1991-1992 catalogs, p. 888 (Grooved PTFE tubing).

*Primary Examiner*—Sam Rimell
*Attorney, Agent, or Firm*—Merchant, Gould, Smith, Edell, Welter & Schmidt

[57] ABSTRACT

An apparatus for use as a catheter guidewire and a method for making a catheter guidewire. The apparatus comprises an elongate non-coiled wire having a proximal portion, a distal tip and a flexible portion located between the proximal portion and the distal tip having axially spaced grooves cut therein. The method for making the guidewire includes burnishing one end of a wire to create a rounded distal tip and cutting a predetermined pattern of axially spaced grooves in a length of wire adjacent to the distal tip to create a flexible portion.

22 Claims, 3 Drawing Sheets

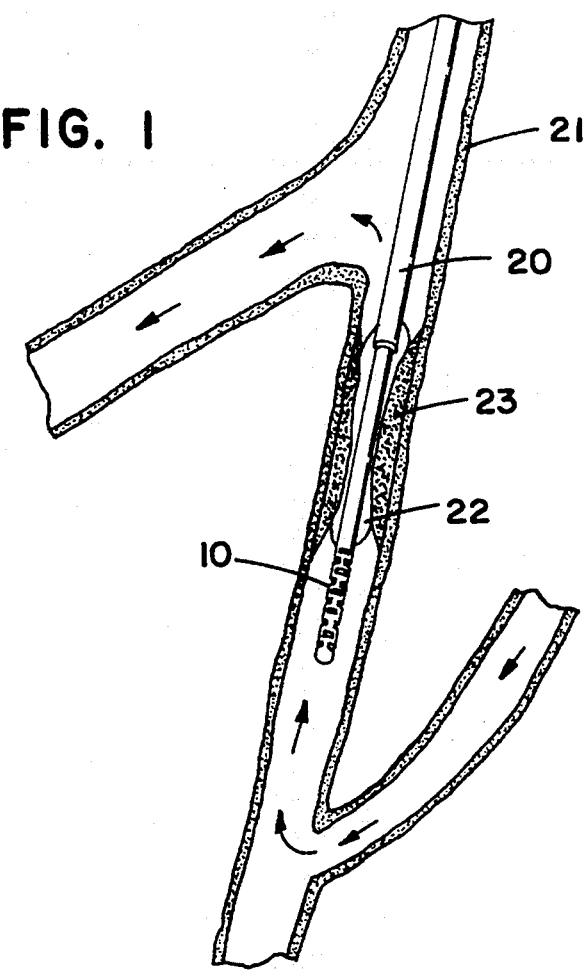
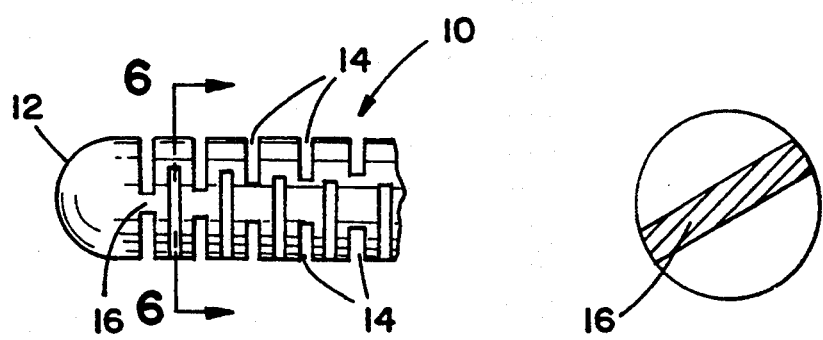

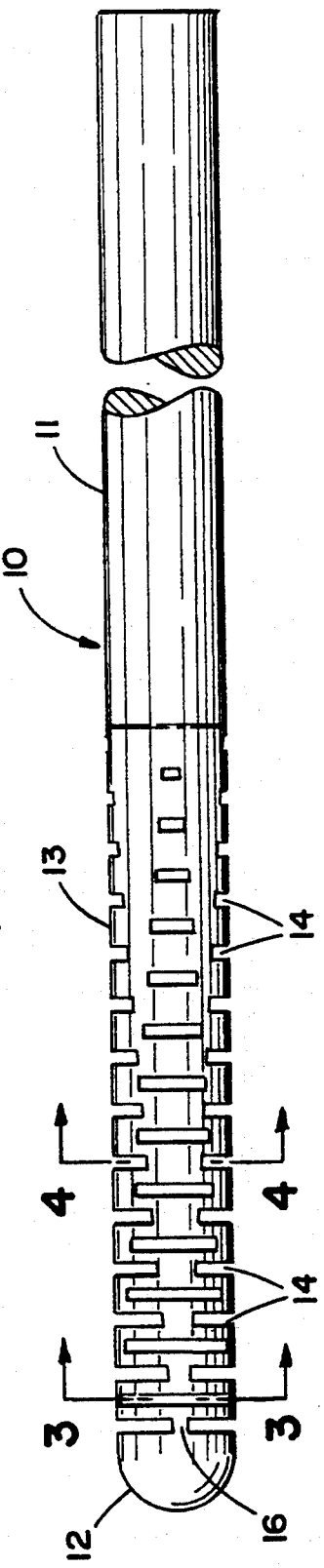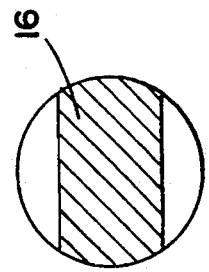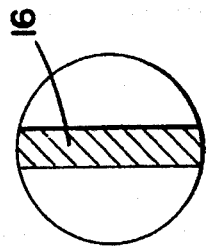

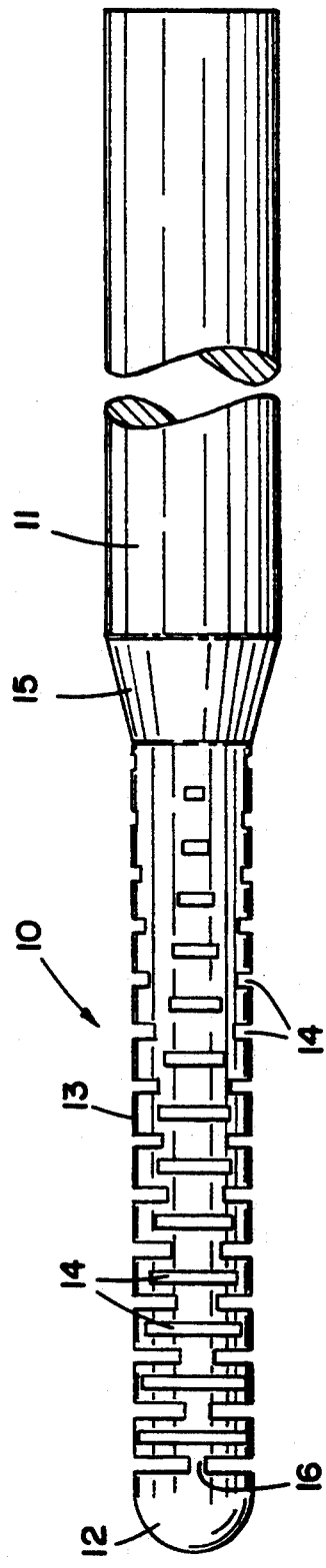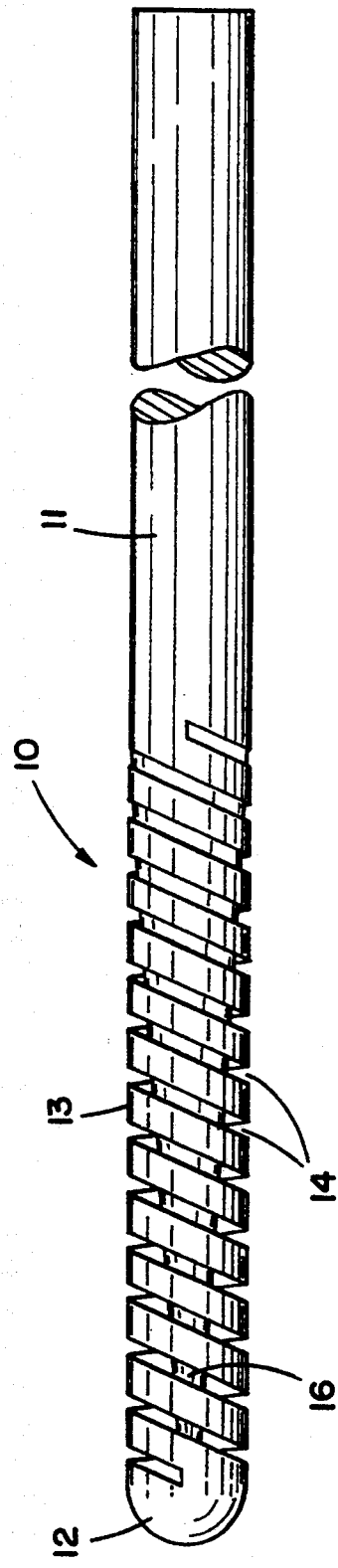

FLEXIBLE CATHETER GUIDEWIRE

FIELD OF INVENTION

The present invention relates to a catheter guidewire and, more particularly, to a guidewire with a flexible tip that is made as a single part.

BACKGROUND OF INVENTION

Catheters are often used for diagnostic or therapeutic procedures that require the insertion of a catheter into the circulatory system to reach a predetermined site such as an artery near the heart. The catheter is positioned at the desired site by alternately advancing a guidewire ahead of the catheter from a body access site, through the circulatory system until reaching the desired site. The path that the guidewire and catheter must follow is tortuous.

The catheter and guidewire must be quite flexible in order to follow the tortuous path to the desired site. However, because these guidewires are advanced through the circulatory system by applying a torque to the proximal end of the guidewire which is located at an external site, the guidewire must have sufficient column strength to allow the distal end of the guidewire to be manipulated from the external access site, which can be more than 150 centimeters from the distal end.

Current catheter guidewire designs attempt to meet these requirements by incorporating a tapered distal end region to increase the flexibility of the guidewire's distal end. Unfortunately, this reduces the column strength of the distal end. To remedy this problem, a wire coil is brazed or soldered onto the tapered section of the wire to increase the column strength of the tapered wire section without losing the flexibility. Guidewires of this type are disclosed in U.S. Pat. Nos. 4,538,622, 4,545,390, 4,582,181 and 4,846,186.

Unfortunately, this type of guidewire construction requires many manufacturing steps including the tapering of the guidewire, the forming of the wire coil, cutting the coil to the desired length and fastening the coil to the distal end section of the guidewire. This method of construction is not only time consuming and costly to manufacture, but it also presents the danger of having the coil separate from the wire while it is in the patient.

One attempt to eliminate the drawbacks of the current designs was to enclose the tapered distal end section in a polymer sleeve as described in U.S. Pat. No. 5,095,915. The addition of the polymeric sleeve is used to increase column strength of the tapered distal end of the catheter guidewire without using a coil. Axially spaced grooves are then cut into the polymeric sleeve to increase the bending flexibility of the sleeve. Unfortunately, this method also requires the use of multiple manufacturing steps and parts to form the guidewire. In addition, there is the potential danger of having the polymeric sleeve separating from the wire within a vessel of the patient. Moreover, because the distal end of the wire is tapered, the strength of the distal end is reduced.

Therefore, there arises a need for a catheter guidewire that is made from a single piece having a flexible distal tip to allow the guidewire to follow the tortuous path and having a sufficient column strength to allow manipulation of the catheter guidewire from an external access site.

SUMMARY OF THE INVENTION

The invention is for an apparatus for use as a catheter guidewire and a method for making a catheter guidewire. The invention includes an elongate non-coiled wire having a proximal portion, a distal tip and a flexible portion having axially spaced grooves cut therein located between the proximal portion and the distal tip. The grooves are cut in a predetermined pattern that will increase the flexibility of the distal end of the guidewire. However, because the guidewire is made from a single piece, the column strength of the flexible portion can be maintained. In addition, because the present invention is made from a single piece, the danger of having portions of the guidewire separate within a vessel of the patient is eliminated.

The process for making a guidewire according to the invention would include the steps of burnishing one end of the wire to create a rounded distal tip and cutting a predetermined pattern of axially spaced grooves in a predetermined length of wire adjacent to the distal tip to create a flexible portion. The guidewire would then be coated with a thin polymer coating such as teflon or hydrogels for slipperiness. The present invention, eliminates the additional parts and many of the manufacturing steps that are related to the prior references, therefore, reducing the cost of the guidewire. The present invention could also be made using computer guided tooling to further reduce the cost of producing the guidewire and increasing the ease of its manufacture.

The present invention is further explained hereinafter with more particularly in reference to the preferred embodiment shown in the following drawings.

BRIEF DESCRIPTION OF THE DRAWINGS

FIG. 1 is a diagrammatical view showing a blood vessel that has been occluded with deposits along the inner wall and showing positioning of a flexible guidewire and catheter within the vessel;

FIG. 2 is an elevational view of the preferred embodiment of the invention with portions broken away;

FIG. 3 is a cross-sectional view of a portion of FIG. 2;

FIG. 4 is a cross-sectional view of a portion of FIG. 2;

FIG. 5 is an elevational view of an alternative embodiment of FIG. 2 with portions broken away;

FIG. 6 is a cross-sectional view of a portion of FIG. 5;

FIG. 7 is an elevational view of a second embodiment of the invention with portions broken away; and FIG. 8 is an elevational view of a third embodiment of the invention with portions broken away.

DETAILED DESCRIPTION OF THE PREFERRED EMBODIMENT

As illustrated in FIG. 1, a small diameter guidewire 10 can be used for routing a catheter 20, such as a balloon catheter 22, through a patient's cardiovascular system to a region having occlusions 23 which have restricted blood flow through a blood vessel 21. The guidewire 10 will have a length sufficient to be routed from an entry point, through the patient's circulatory system to the obstructed blood vessel 21 region. The length of these guidewires 10 can typically range from 175 centimeters to 300 centimeters and generally have outer diameters from 10–18 mils (thousandths of an inch). As the guidewire 10 is inserted along the circulatory system, a catheter 20 with a center passageway or lumen having a sufficient diameter to accommodate the guidewire 10 is then slid over the guidewire 10. The guidewire 10 and catheter 20 are then alternately advanced through the circulatory system until reaching the desired location. The physician conducting the procedure monitors the progress of the guidewire 10 on an X-ray viewing screen.

Guidewires 10 are also used for peripheral use, i.e. for accessing locations other than coronary arteries. These guidewires 10 have characteristics similar to guidewires 10 for coronary use, but they typically have lengths from 80 centimeters to 400 centimeters and outer diameters from 10-65 mils, however, more typically 25-38 mils. Those skilled in the art would recognize that, except for size, the operation of and characteristics of coronary and peripheral use guidewires are very similar. Therefore, the following discussion is limited to guidewires 10 for coronary use with the understanding that the following discussion is also applicable to guidewires 10 for peripheral uses.

The distal end of the guidewire 10 is flexible and can be formed in a predetermined shape to facilitate routing the guidewire 10 through the circulatory system to the obstructed blood vessel 21. The attending physician advances the guidewire 10 through the circulatory system by applying torques to the proximal end of the guidewire 10. These torques are transmitted along the length of the guidewire 10 and reorient the distal end to point in the desired direction.

As shown in FIGS. 2 through 4, the guidewire 10 has a proximal portion 11, a distal tip 12, and flexible portion 13. As stated earlier, a guidewire 10 for coronary uses would have an outer diameter from 10-18 mils (thousandths of an inch). In the preferred embodiment, the guidewire 10 would be made from a kink resistant material such as nitinol. Nitinol is preferred because of its superelasticity characteristics. This superelasticity characteristic resists kinking, thereby enabling the guidewire 10 to bend around sharp radius turns without becoming permanently deformed. Nitinol also has greater torquability than conventionally used materials, thereby increasing the steerability of the guidewire 10. However, those skilled in the art would recognize that other materials, such as stainless steel or the like, could be used with the invention.

The distal tip 12 is located at one end of the guidewire 10 and has a semi-spherical shape. In the preferred embodiment, the distal tip 12 would have a diameter of at least 10 mils to prevent the distal tip 12 from damaging the vessel 21. A distal tip 12 with a diameter less than 10 mils could act like a spear to damage or puncture the vessel 21. The distal tip 12 would also be plated with a radio opaque material, such as gold, to enable the practitioner to view the distal tip 12 on an X-ray viewing screen. In the preferred embodiment, the distal tip 12 could be plated with 0.2-0.5 mils of gold.

The flexible portion 13 would have a first end adjacent to the proximal portion 11 and a second end adjacent to the distal end 12 and would contain a predetermined pattern of axially spaced grooves 14. In the preferred embodiment, as shown in FIGS. 2-4, non-circumferential grooves 14 would be cut into the flexible portion 13 from oppositely displaced directions along a plane extending through a cross-section of the flexible portion 13. The grooves 14 would also be cut such that adjacent grooves 14 would be cut from directions that are offset by 90 degrees. Those skilled in the art would recognize that adjacent grooves 14 could be offset by other angles, such as 30 degrees as illustrated in FIGS. 5 and 6, and that grooves 14 could be cut along multiple axes.

In addition, as illustrated in FIGS. 3 and 4, the grooves 14 located adjacent to the first end of the flexible portion 13 would have a depth less than the grooves 14 located adjacent to the distal tip 12. By increasing the depth of the grooves 14 near the distal tip, the flexibility of the flexible portion 13 nearest the distal tip 12 is increased. While FIG. 2 illustrates a pattern of grooves 14 cut with slightly increasing depths to create a smooth tapered core 16 in the flexible portion 13, those skilled in the art would recognize that the grooves 14 could be cut to create a flexible portion 13 with a stepped tapered core 16.

In the preferred embodiment, the flexible portion 13 would have a length between 5-30 cm, more preferably 20-25 cm, and the width of the grooves 14 and spaces between the grooves 14 would be between 5-10 mils. To preserve the column strength of the flexible portion 13, the depth of the grooves 14 would be restricted such that the minimum thickness of the core 16 in the flexible portion 13 would be between 3 and 5 mils.

As shown in FIG. 7, a second embodiment of the invention would include a tapered portion 15 between the proximal portion 11 and the flexible portion 13. The tapered portion 15 would be used to reduce the diameter of the proximal portion 11 to a diameter of no less than 10 mils. The outer diameter of the flexible portion 13 and distal tip 12 would then be maintained at approximately 10 mils for the reasons stated previously. The flexible portion 13 and distal tip 12 could then be arranged and configured according to the previously disclosed preferred embodiment.

As shown in FIG. 8, a third embodiment of the invention would contain a flexible portion 13 having helical grooves 14 cut therein. These helical grooves 14 could be of a uniform depth or of an increasing depth when moving toward the distal tip 12. The width of the grooves 14 is preferably between 5 and 10 mils and the width of the spacing between the grooves 14 is preferably between 5 and 20 mils. Those skilled in the art would recognize that this embodiment could also incorporate a tapered portion 15 as disclosed in the second embodiment. Those skilled in the art would also recognize that other groove patterns could be utilized with the present invention, such as circumferential grooves 14 cut to a uniform depth or to increasing depth when moving toward the distal tip 12 or any other pattern that would increase the flexibility of the flexible portion 13.

The preferred method for making a guidewire 10 according to the invention would begin by obtaining a kink resistant wire of the desired length with a diameter between 10 and 18 mils. One end of the wire would then be burnished or ground to form a rounded distal tip 12. If a tapered portion 15, as disclosed in the second embodiment was desired, the diameter of the distal tip 12 and diameter of the length of wire for the flexible portion 13 would be ground to a diameter not less than 10 mils. A gradual taper would then be ground between the first end of the flexible portion 13 and the outer diameter of the remaining proximal portion 11.

A predetermined pattern of grooves 14 would then be cut into the flexible portion 13 by any suitable machining method, such as grinding, electrostatic discharge machining (EDM), lasers or the like. However, the preferred method for cutting the grooves 14 would be to use a computer guided EDM machine, and even more preferably, a computer guided plunge EDM machine. As recognized by those skilled in the art, a plunge EDM machine utilizes charged electrodes that are arranged and configured to cut a predetermined shape into a base material.

To cut the grooves 14 using the plunge EDM machine, the distal tip 12 and the proximal portion 11 of the guidewire 10 would be fastened to a holding device such that the flexible portion 13 is positioned between one or more pairs of oppositely disposed electrodes at the desired location for cutting a groove 14. Each pair of oppositely disposed electrodes would have a configuration designed to cut a desired groove shape and depth. One electrode from each pair would be plunged into the guidewire 10 to cut a portion of the groove 14. The electrode would be removed and then the oppositely disposed electrode would be plunged into the guidewire to complete the groove 14. Those skilled in the art would recognize that a series of electrode pairs could be disposed along the length of the flexible portion 13, each being configured to cut a particular groove shape at a particular location. Such a system could permit the cutting of all of the grooves 14 for a flexible portion 13 in a two-step process, enabling the improved guidewires 10 to be manufactured in a high speed, reliable and repeatable manner.

Those skilled in the art would also recognize that a wire EDM machine could also be used. A wire EDM machine is similar to the plunge EDM machine except that electrically charged wires are used instead of electrodes. Like the previous discussion, cutting the grooves 14 with a wire EDM machine would begin by fastening the guidewire 10 in a holding device and positioning the guidewire 10 at the desired location for cutting a groove 14. The EDM wires would then be moved inward to cut the desired groove 14. The EDM wires would then translate outward beyond the outer diameter of the guidewire 10. The holding device would then rotate and/or translate the guidewire 10 to the desired position for cutting another set of grooves 14. The EDM wires would then be moved inward to cut the next set of grooves 14. This procedure would be repeated throughout the length of the desired flexible portion to cut the desired grooves 14. Those skilled in the art would recognize that multiple holding devices and/or multiple EDM wires could be used to simultaneously cut multiple grooves 14 into multiple guidewires 10.

The distal tip 12 would then be plated with gold by an electroplating process, sputtering or any other plating method. The guidewire 10 would then be coated with a polymer, preferably polyurethane or teflon, to encase the guidewire 10 within a plastic jacket to increase its mobility within a vessel 21. The polymer coating could be applied in one of any well-known methods, such as dip coating, heat shrinking, spray depositing, or vapor depositing the polymer material to the guidewire 10. The guidewire 10 would then be dip coated into a hydrogel and solvent solution to further increase the mobility of the guidewire 10 within the patient. Those skilled in the art would recognize that the guidewire 10 could be coated with other materials, such as polyethylene or other polymers or drug impregnated coatings, to improve its mobility within the patient.

Although characteristics and advantages, together with details for structure, materials, function and process steps, have been described in reference to a preferred embodiment herein, it is understood that the disclosure is illustrative. To that degree, various changes made especially to matters of shape, size and arrangement, to the full extent extended by the general meaning of the terms in which the appended claims are expressed, are within the principles of the present invention.

What is claimed is:

1. A guidewire with a flexible distal end for use with catheters or the like comprising:
    a metal wire having a proximal portion, a distal tip and a flexible portion therebetween, the flexible portion having a plurality of grooves formed in the metal wire so as to provide a desired flexibility, the grooves increasing in depth toward the distal tip to create a generally tapered core.

2. A guidewire according to claim 1, wherein the metal wire is made of nitinol.

3. A guidewire according to claim 1, wherein the core of the flexible portion has a continuously sloped taper.

4. A guidewire according to claim 1, wherein the guidewire further comprises a polymer coating over the metal wire to increase the mobility of the guidewire.

5. A guidewire according to claim 4, wherein the guidewire further comprises an outer hydrogel coating over the polymer coating.

6. A guidewire according to claim 1, wherein the guidewire includes a central axis and the plurality of grooves comprise non-circumferential axially spaced grooves formed generally perpendicular to the central axis.

7. A guidewire according to claim 6, wherein adjacent non-circumferential axially spaced grooves are offset by an angle.

8. A guidewire according to claim 1, wherein the guidewire further comprises a tapered portion between the proximal and flexible portions having a decreasing diameter toward the flexible portion.

9. A guidewire according to claim 1, wherein the distal tip is plated with a radiopaque material.

10. A guidewire with a flexible distal end for use with catheters or the like comprising:
    a. a continuous metal wire having a proximal portion, a distal tip having a rounded end and a flexible portion generally located between the proximal portion and distal tip, the flexible portion having axially spaced grooves formed in the metal wire that are arranged and configured to create a core in the flexible portion that tapers inward toward the distal tip; and
    b. coating means to increase the mobility of the guidewire.

11. A guidewire according to claim 10, wherein the coating means is a polymer coating applied to the guidewire which is covered with a hydrogel coating.

12. A process for making a guidewire with a flexible distal end for use with catheters or the like comprising the steps of:
    a. providing a metal wire having a distal tip;
    b. cutting a plurality of axially spaced grooves in the metal wire along a length of the wire adjacent the distal tip; and
    c. increasing the depth of the grooves toward the distal tip to create a flexible portion of the distal end of the guidewire.

13. A process for making a guidewire according to claim 12, wherein the grooves are cut using an electrostatic discharge machining tool.

14. A process for making a guidewire according to claim 12, wherein the length of the flexible portion having the axially spaced grooves is between 5 and 30 cm and the width and spacing of the axially spaced grooves is about between 5–10 mils.

15. A process for making a guidewire according to claim 12, wherein the grooves are cut to be non-circumferential with adjacent grooves offset by an angle.

16. A process for making a guidewire according to claim 12, wherein the process further comprises the step of grinding the flexible portion to create a flexible portion with a diameter less than a diameter of a proximal portion; and grinding a tapered portion between the flexible portion and the proximal portion.

17. A process for making a guidewire with a flexible distal end for use with catheters or the like comprising the steps of:
 a. providing a continuous metal wire having a distal tip;
 b. burnishing the distal tip to a rounded shape;
 c. cutting a predetermined pattern of axially spaced grooves in the metal wire along a predetermined length of the wire adjacent to the distal tip to create a flexible portion of the distal end of the guidewire;
 d. coating the guidewire with a polymer to increase the mobility of the guidewire; and
 e. plating the distal tip with a radiopaque material to enable the guidewire to be viewed on an x-ray.

18. A process for making a guidewire according to claim 17, wherein the guidewire is coated by dipping the guidewire in a liquid polymer to create a plastic jacket over the guidewire; and then dipping the guidewire with the plastic jacket into a hydrogel solution to form an outer coating.

19. A guidewire according to claim 6, wherein the length of the flexible portion is between 15–30 cm and the width and spacing of the axially spaced grooves are about between 5–10 mils.

20. A guidewire according to claim 1, wherein the plurality of grooves comprise a continuous helical groove along the flexible portion.

21. A guidewire according to claim 12, wherein the grooves are cut with a laser.

22. A guidewire according to claim 12, wherein the process further comprises the step of burnishing the distal tip of the metal wire so that it is rounded.

* * * * *